United States Patent [19]
Mondet et al.

[11] Patent Number: 5,519,063
[45] Date of Patent: May 21, 1996

[54] OILY COSMETIC COMPOSITION CONTAINING, AS A THICKENER, AN ASSOCIATION OF TWO COPOLYMERS AND OPTIONALLY CONTAINING AN AMPHIPHILIC RHEOLOGY CORRECTOR

[75] Inventors: Jean Mondet, Drancy; Bertrand Lion, Livry Gargan; Didier Candau, Melun; Pascal Simon, Vitry-Sur-Seine, all of France

[73] Assignee: L'Oreal, Paris, France

[21] Appl. No.: 30,197

[22] PCT Filed: Jul. 24, 1992

[86] PCT No.: PCT/FR92/00734

§ 371 Date: May 10, 1993

§ 102(e) Date: May 10, 1993

[87] PCT Pub. No.: WO93/01797

PCT Pub. Date: Feb. 4, 1993

[30] Foreign Application Priority Data

Jul. 25, 1991 [FR] France ................... 91 09438

[51] Int. Cl.⁶ ................ A61K 7/48; A61K 7/06
[52] U.S. Cl. ................ 514/772.4; 514/772.6; 514/844; 514/938; 525/203
[58] Field of Search ................ 514/772.3, 772.4, 514/772.6, 844, 938, 941, 942; 525/191, 203, 206

[56] References Cited

U.S. PATENT DOCUMENTS

| | | | |
|---|---|---|---|
| 4,839,166 | 6/1989 | Grollier et al. | 424/71 |
| 4,842,849 | 6/1989 | Grollier et al. | 424/70 |

FOREIGN PATENT DOCUMENTS

| | | |
|---|---|---|
| 140274 | 5/1985 | European Pat. Off. . |
| 268164 | 5/1988 | European Pat. Off. . |
| 406042 | 1/1991 | European Pat. Off. . |
| 2238474 | 2/1975 | France . |
| 2305969 | 10/1976 | France . |
| 2305967 | 10/1976 | France . |
| 0406042 | 1/1991 | France . |

*Primary Examiner*—Jeffrey Mullis
*Attorney, Agent, or Firm*—Cushman Darby & Cushman

[57] ABSTRACT

Use in association, as oil thickners, in a cosmetic composition comprising an oily phase, of at least one first copolymer including patterns derived from at least one lipophilic monomer and patters derived from at least one hydrophilic monomer, comprising at least one carboxylic acid or sulphonic grouping, and of at least one second copolymer including patterns derived from at least one lipophilic monomer and patterns derived from at least one hydrophilic monomer comprising at least one amine, amide, alcohol or ether grouping. Said first and second copolymers have a molecular weight of not less than approximately 100 000. The association enables thickened composition to be obtained, the texture, look and feel of which correspond to a cosmetic use.

14 Claims, No Drawings

OILY COSMETIC COMPOSITION CONTAINING, AS A THICKENER, AN ASSOCIATION OF TWO COPOLYMERS AND OPTIONALLY CONTAINING AN AMPHIPHILIC RHEOLOGY CORRECTOR

This invention relates to the use in association, as a thickening agent for an oily cosmetic composition, of two copolymers having distinct units.

Numerous cosmetic compositions are known which are intended, principally, to be applied to the skin, lips, eyelashes and hair, and which are provided in the form of oily solutions or in the form of emulsions. The preparation of these compositions generally requires thickening the oily phase principally to facilitate their application.

It is also necessary to thicken the oily phase when it is desired to obtain a composition in the form of a gel, for example, an anhydrous gel. The formulation, in the form of an anhydrous gel, is employed when the substances present in the composition are sensitive to humidity and/or to the oxygen of the air. Moreover, it is known that oils have very interesting cosmetic properties (principally cleansing, makeup removal and emollient properties), but that their use is not convenient because they are too fluid. In fact, their application is only slightly satisfactory when they are provided in the form other than a thick oily composition or gel.

A known method of thickening oily compositions consists in incorporating a wax in the oily phase. However, compositions thickened with a wax have a feel which is generally considered disagreeable.

There has also been employed oil thickening techniques based on the incorporation of silicas, bentones or metallic salts of fatty acids, (for example aluminum salts) or of esterification derivatives of sugars, (for example dextrine palmitate) etc.

However, none of these procedures provides a composition possessing both the transparency and consistency of a gel.

It has now been discovered that it is possible to obtain a thickening, which is principally capable of reconciling these requirements, in the production of cosmetic compositions, notwithstanding the nature of the oil or mixture of oils employed.

It has also been discovered that the rheologic and cosmetic properties of the compositions thus obtained can be modified and improved, if desired, by using a rheologic corrector agent, and principally certain amphiphilic agents, as detailed more fully below.

The gels obtained in accordance with the invention do not have a brittle texture, that is to say, that they can be removed easily with the finger by adherence to it and they do not have a stringy texture, that is to say, they do not flow in a viscous stream as does, for example, liquid honey.

One of the advantages of the use of polymers for thickening cosmetic compositions is that they do not pass through the cutaneous barrier, so that there is no need to fear systemic toxicity.

Another advantage of the use of polymers is that it is possible to obtain significant thickening with a relatively small amount of the thickening agent.

Moreover, the advantage of the use of a system based on the combination of two polymers is that each of the polymers, before mixing, gives fluid solutions, which facilitate preparation techniques, by avoiding principally significant dissolution times and by avoiding the presence of insoluble impurities in the medium after mixing.

The present invention thus relates to a thickening agent for oils in a cosmetic composition comprising an oily phase, the said thickening agent comprising at least a first copolymer comprising units derived from at least one lipophilic monomer and units A derived from at least one hydrophilic monomer comprising at least one carboxylic or sulfonic acid group, and at least a second copolymer comprising units derived from at least one lipophilic monomer and units B derived from at least one hydrophilic monomer comprising at least an amine, amide, alcohol, or ether group, the said first and second copolymers having a molecular mass not lower than about 100,000.

In particular embodiments, the use of the thickening agent according to the invention can also exhibit the following characteristics, taken singly or, the case being, in combination:

- in the said first and second copolymers, the weight amount of units derived from the lipophilic monomer is at least equal to 50%;
- in the said first and second copolymers, the weight amount of the A units and the B units, respectively, is at least equal to 2%;
- the said A units are derived from at least one monomer selected from among unsaturated carboxylic and sulfonic acids;
- the said unsaturated carboxylic acids comprise: unsaturated carboxylic monoacids and unsaturated carboxylic diacids, their monoesters and their monoamides;
- the said unsaturated carboxylic monoacids are selected from among acrylic acid, methacrylic acid and crotonic acid, and/or the said diacids are selected from among maleic acid and itaconic acid, and/or the said monoesters or monoamides are derived, respectively, from alcohols or amines having from 1–22 carbon atoms;
- the said unsaturated sulfonic acids are selected from among 2-acrylamido-2-methyl propane sulfonic acid and 2-sulfoethyl methacrylate;
- the said B units are derived from at least one hydrophilic monomer comprising an amine group having the formula:

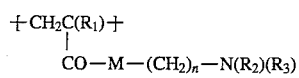

wherein:

M represents —O— or —NH—, $R_1$ represents —H or —$CH_3$, n is a number from 2 to 20, $R_2$ and $R_3$, each independently, represent —H or a hydrocarbon group having 1–4 carbon atoms;

- the said B units are derived from monomers selected from among dimethylaminoethyl methacrylate, diethylaminoethyl acrylate and N-dimethylaminopropyl methacrylamide;
- the said B units are derived from at least one unsaturated hydrophilic monomer comprising an amide group, selected from among acrylamide, methacrylamide, N,N-dimethylacrylamide, N-vinyl pyrrolidone and diacetone acrylamide;
- the units, derived from lipophilic monomers, which are present in the two types of copolymers employed according to the invention, can be units derived from monomers used in a conventional manner, principally in cosmetology, when it is desired to introduce lipophilic units in a polymer. These monomers are, for example, esters derived from unsaturated acids and long chain fatty alcohols, principally stearyl or lauryl acrylates or methacrylates;

the said copolymers have a molecular mass at least equal to 200,000;

the relative weight amounts of the said first and second copolymers in the said combination, are in the range of 10:90 to 90:10 and in particular in the range of 25:75 to 75:25;

the total concentration of the said first and second copolymers in the said composition is less than 10 percent and in particular less than 5 percent by weight;

the total concentration of the said copolymers must be sufficient to obtain the desired degree of thickening which is, however, variable according to the case; generally the total concentration of the said copolymers is greater than 0.1 percent by weight, and can vary, in particular, from 0.5 to 5 percent; generally, when the total concentration of the said copolymers reaches about 2 to 3 percent, a gelled oil (having a gel texture) is obtained.

In accordance with the invention, the oily phase generally contains at least 55 percent, and preferably at least 75 percent by weight of oil.

To obtain, in accordance with the invention, thick cosmetic compositions, a solution of one of the polymers previously dissolved in a portion of the oil or a mixture of oils to be thickened, is mixed with a solution of another polymer in another portion of the oil or mixture of oils to be thickened.

Preferably, the other liposoluble ingredients of the composition are added, each copolymer is dissolved in a portion of the oil, or mixture of oils, to be thickened, and the two resulting solutions are mixed.

With the exception of this particularity, the thick cosmetic compositions obtained in accordance with the invention are prepared in accordance with conventional methods.

When the final compositions are emulsions, in particular water-in-oil (w/o) emulsions, the oily phase, as indicated above, is prepared before preparing the emulsion with an aqueous phase.

It has also been discovered that it is possible to improve the properties of the resulting thick oily compositions, when considered necessary or desirable, by using a rheology corrector agent. This is the case principally when the resulting gel is too viscous and has a tendency to crack, or when it is less viscous but only slightly flexible and very stringy. It has been discovered principally that certain nonionic amphiphilic agents are capable of improving the rheologic and cosmetic properties of the compositions of the invention, by imparting to them a rheologic behavior of the pseudo-plastic type which permits to develop low velocity gradient of the constraints compatible with the solidification of the product and with its spreadability. By constraints is meant the force that opposes the product to an exterior influence, and by velocity gradient is meant the spatial variation of the speed of deformation of the product. Prehensile and nonstringy gelled textures are thus obtained. Without introduction of the amphiphilic agent, the constraints developed at low gradient risk being either high, characterizing a solid and brittle gel, or weak, characterizing a stringy gel. Due to the invention, textures that are particularly well adapted to cosmetic products, particularly prehensile and nonstringy gels are obtained.

The compositions of the invention can then contain a rheologic corrector agent which is principally a nonionic amphiphilic agent having an HLB value between about 12 and 40. This amphiphilic agent is preferably employed in hydrated form, that is to say, in the presence of a certain amount of water and, optionally, in the presence of a water-soluble alcohol. The water-soluble alcohol is, for example, ethanol, isopropanol, or a polyol such as glycerol, propylene glycol, 1,3-butanediol, sorbitol, glucose, etc. The nonionic amphiphilic agents useful as rheologic corrector agents, according to the invention, can be selected principally from among:

polyoxyethylenated esters of fatty acids and sorbitan, polyoxyethylenated esters of fatty acids and glycerol, polyoxyethylenated esters of fatty acids and propylene glycol, polyoxyethylenated or polyoxypropylenated alkyl ethers, polyoxyethylenated or polyoxypropylenated alkyl phenyl ethers, and polyoxyethylenated Guerbert alcohols.

The amphiphilic compounds mentioned above are known compounds.

Guerbert alcohols are alcohols having the formula:

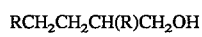

wherein

R principally represents a long chain alkyl group, for example, a 2-octyl dodecyl group. The polyoxyethylenated ethers of these alcohols are prepared in accordance with conventional methods.

The nonionic amphiphilic agents are introduced in an amount sufficient to impart the desired rheologic properties. This sufficient amount can be determined in each case by simple routine experimentation. Generally this amount represents from 1 to 10 weight percent, most often from 4 to 6 weight percent, based on the weight of the oily phase.

It is appropriate to note that the amount of water mentioned here is the amount of water used for the hydration of the amphiphilic agent, that is to say, the water introduced at the same time as the nonionic amphiphilic agent. The final composition naturally can contain more significant amounts of water when it is provided in the form of an emulsion.

The compositions of the invention, containing a rheologic corrector agent mentioned above, are then principally those whose oily phase contains (weight percent, total 100 percent):

thickening mixture of copolymers: 0.5–10% (preferably 2–4%), nonionic amphiphilic agent: 1–10% (preferably 4–6%), water: 1–10% (preferably 4–6%), oil: 55–95% (preferably 75–85%) and optionally: water-soluble alcohol: 1–10% (preferably 2–6%).

To prepare these compositions, the oily phase containing the copolymers can be heated before its introduction into the nonionic amphiphilic agent, preferably hydrated and containing optionally an alcohol. A single one of the copolymers in oil can be added before introduction into the amphiphilic agent and it can then be completed with the second copolymer.

The effect observed with the nonionic amphiphilic agent, in the presence of the mixture of thickening copolymers, is surprising because, in the absence of the said copolymers, the amphiphilic agent at the concentration at which it is used, does not permit gelling of the oil: there is decantation and recrystallization of the amphiphilic agent. Also, the rheologic effect of the nonionic amphiphilic agent is not observed when it is used in the presence of another oil thickening system, such as dextrin palmitate or salts of fatty acid and aluminum.

The oils employed alone or in mixture in the compositions obtained in accordance with the invention can be principally:

- hydrocarbons, comprising mineral oils such as paraffin oil, petrolatum oil, hydrogenated polyisobutylene such as that sold by Nippon Oil under the mark "PARLEAM", branched hydrocarbons such as those sold under the designation "ISOPAR";
- triglycerides, in particular vegetable oils, such as turnsol oil, sesame oil, colza oil, sweet almond oil, calphyllum, palm oil, avocado oil, jojoba oil, olive oil, ricin oil, or cereal germ oils such as wheat germ oil;
- various oily esters derived from long chain acid and/or alcohol, such as Purcellin oil, isopropyl myristate, butyl myristate, cetyl myristate, isopropyl palmitate, butyl palmitate, 2-ethylhexyl palmitate, isopropyl stearate, butyl stearate, octyl stearate, hexadecyl stearate, isocetyl stearate, decyl oleate, hexyl laurate, propylene glycol dicaprylate, di-isopropyl adipate and mixtures of $C_{12}$ and $C_{15}$ benzoic esters sold under the designation "FINSOLV TN" by Witco, etc;
- animal oils such as perhydrosqualene;
- silicone oils such as dimethylpolysiloxanes, phenyldimethicones, cyclomethicones, alkyldimethicones, etc;
- long chain alcohols such as oleic alcohol, linoleic alcohol, linolenic alcohol, isostearyl alcohol or octyl-dodecanol;
- esters derived from lanolic acid such as isopropyl or isocetyl lanolate;
- acetylglycerides, the octanoates and decanoates of alcohols or polyalcohols (principally glycol or glycerol), and the ricinoleates of alcohols or polyalcohols, for example cetyl ricinoleate.

There can be incorporated with the oils, various lipophilic substances called actives, beneficial for the skin, such as tocopherol and its esters, fatty esters of ascorbic acid, 18-betaglycyrrhetinic acid, ceramides, ultraviolet absorbing filter substances, antioxidants, etc.

One of the characteristics of the thickening copolymers used in accordance with the invention is that they are soluble in oils generally employed in cosmetic compositions, with the exception of certain silicone oils employed alone.

Preferably, the silicone oils and vegetable oils rich in triglycerides are used in admixture with at least 10 percent of another oil (principally a mineral oil or an ester of a fatty acid or fatty alcohol).

The invention also relates to a cosmetic composition comprising a thick oily phase due to the combination of two copolymers such as defined previously.

The invention also relates to a composition thus thickened containing, moreover, a rheologic corrector agent such as defined above.

The compositions according to the invention constitute, principally, anhydrous compositions (anhydrous oils, sticks or gels), gelled oils, or even water-in-oil or oil-in-water emulsions.

The compositions of the invention constitute, for example, makeup remover oils, lip rouge, anhydrous mascaras, perfumed gels or oils, capillary treating oils (anti-hair loss, antipellicular, defrizzing, etc.), pre-bronzing gels or oils, solar gels or oils, solar sticks, deodorant sticks, oily deodorant gels, aromatic oily gels for the care of the mouth (with or without bacteriacides), foaming oils for the hair or bath, and complexion foundations.

The following nonlimiting examples illustrate the invention.

EXAMPLES OF PREPARATION

Example 1

Synthesis of copolymers by solution polymerization General method:

In a 500 ml reactor fitted with a central mechanical stirrer, a thermometer, a condenser and a nitrogen lead-in tube, there are successively added, the monomers, solvent or mixture of solvents and finally, the polymerization initiator. The mixture is stirred at ambient temperature to obtain a homogeneous solution. Nitrogen is bubbled into the reaction which is then heated to the desired reaction temperature; the elevation of the temperature is accomplished in 30 minutes. There are then maintained stirring of the reaction mixture, the introduction of nitrogen and the selected reaction temperature for 10 hours. The temperature of reaction medium is then lowered to ambient temperature and the polymer is purified by precipitation in a nonsolvent of the product formed but a good solvent for the remainder of the nonreacted monomers.

The polymer is then oven dried under a vacuum at a temperature lower than or equal to 80° C. until a constant weight is achieved.

The monomers employed are designated by the following abbreviations:

LAUA: lauryl acrylate
MAA: methacrylic acid
SMA: stearyl methacrylate
AA: acrylic acid
DAMEMA: Dimethylaminoethyl methacrylate
DAEA: diethylaminoethyl acrylate
NVP: N-vinyl pyrrolidone
AM: acrylamide
EHMA: ethyl hexyl metacrylate
NDAM: N-dodecylacrylamide
NTBA: N-t.butyl acrylamide
NTOA: N-t. octyl acrylamide
ITAN: itaconic anhydride
DAAM: diacetone acrylamide The initiator employed is azo bis-isobutyronitrile at a concentration of 0.5 to 0.7 percent.

The solvents used are mixtures of toluene and ethanol except for Example 13 (tetrahydrofuran).

The precipitating agent is ethanol, except for Examples 10–12, methanol in Examples 10 and 12; and a 50:50 mixture of methanol and water in Example 11.

The reaction temperature is 60° C. (Examples 1–3) or 65° C. (Examples 4–14).

The results are set forth in Table I below.

The indication T:x% means that there is employed, as solvent, a toluene-ethanol mixture containing x% of toluene, and then (100-x)% of ethanol

TABLE 1

| Examples No. | Monomers | | Solvent | Concentration monomers | Yield |
|---|---|---|---|---|---|
| 1 | SMA<br>MAA | 95%<br>5% | T =74% | 57% | 97% |
| 2 | SMA<br>DAMEMA | 95%<br>5% | T =74% | 57% | 90% |
| 3 | LAUA<br>MAA | 95%<br>5% | T =74% | 57% | 90% |
| 4 | SMA<br>AA | 93%<br>7% | T =74% | 59% | 87% |
| 5 | SMA<br>AA | 96%<br>4% | T =74% | 59% | 89% |
| 6 | SMA<br>DAEA | 83%<br>17% | T =86% | 59% | 83% |
| 7 | SMA<br>NVP | 86%<br>14% | T =86% | 59% | 84% |
| 8 | SMA<br>AM | 96.5%<br>3.5% | T =76.5% | 54% | 92% |
| 9 | HEMA<br>DAMEMA | 93.7%<br>6.3% | T =85% | 55.5% | 90% |
| 10 | NDAM<br>DAMEMA | 94%<br>6% | T =85% | 55.5% | 74% |
| 11 | NTBA<br>DAMEMA | 94%<br>6% | T =65% | 42% | 84% |
| 12 | NTOA<br>DAMEMA | 94%<br>6% | T =58% | 39% | 92% |
| 13 | SMA<br>ITAN | 94.4%<br>5.6% | THF | 59% | 90% |
| 14 | SMA<br>DAAM | 75%<br>25% | T =73% | 57% | 91% |

Example 15

Suspension polymerization

Into a reactor 250 g of distilled water, 2.5 g of hydroxyethylcellulose and 0.13 g of mercaptoethanol are introduced. The dissolution is effected with stirring and nitrogen bubbling. The mixture is then heated to 80° C. With stirring 95 g of SMA preheated to 40° C. and 5 g of MAA are then introduced.

At the end of 5 minutes, 0.5 ml of 2-t.butylperoxyethyl hexanoate is added.

At the end of 8 hours at 80° C., the temperature is returned to ambient temperature by cooling with stirring. The reaction mixture is filtered and the resulting beads are washed twice with 1 liter of water containing 0.4% of sodium lauryl sulfate, then with distilled water and dried.

Yield: 90[{]jf44a

Example 16

Suspension polymerization

Into a reactor, 250 g of distilled water, 50 g of sodium chloride, 4 g of hydroxyethylcellulose and 0.16 g of mercaptoethanol are introduced. The reaction mixture is dissolved with stirring and nitrogen is bubbled in. The mixture is heated to 80° C. at which point 90.8 g of SMA preheated to 40° C. and 9.2 g of DAMEMA are introduced. At the end of 5 minutes of stirring, 0.5 ml of 2-t.-butylperoxyethyl hexanote is added. The process is completed as indicated in the preceding example.

Yield: 78%

Example 17

Emulsion polymerization

Into a reactor, 298 g of distilled water and 4 g of hydroxyethylcellulose are introduced. The mixture is dissolved with stirring and nitrogen is bubbled in. The mixture is heated to 50° C. and then 46 g of vinyl stearate, 5.8 g of crotonic acid and 2.5 g of lauroyl peroxide are introduced. The reaction medium is heated to 75° C. for 15 hours at which point it is returnd to ambient temperature. The beads are filterd and washed twice in a liter of water. The polymer, after drying, is obtained with a yield of 86%.

Examples 18–20

In a similar manner, by solution polymerization, copolymers PA1 and PA2 the composition of which is given in Examples F24–F27 below, are prepared.

EXAMPLES OF FORMULATIONS

For each of the examples of formulations described below, the procedure is the following: initially one of the polymers is dissolved in a portion of the mixture of oils contemplated, by heating if it is necessary to accelerate dissolution.

The other polymer is dissolved in the same manner in another portion of the oil mixture. The two resulting solutions are mixed so as to obtain a thickened medium. The other optional ingredients are then added.

Example F1

Thickened capillary foaming oil

This composition has the following formulation:

| | |
|---|---|
| Polymer according to Example 15 | 1.0 g |
| Polymer according to Example 16 | 1.0 g |
| 50/50 monoisopropanolamine lauryl ether sulfate/diethanolamide of copra acid mixture, sold under the designation "TEXAPON WW 99" by Henkel | 35.0 g |
| Light petrolatum oil, HZ NO. 25, sold by Geeraert Matthys | 25.0 g |
| 4-tert.butyl hydroxyianisole | 0.05 g |
| 4-ditert. butyl hydroxytoluene | 0.05 g |
| Propyl parahydroxybenzoate | 0.2 g |
| Decolorized raffinated colza oil, sufficient amount for | 100 g |
| Viscosity of the composition - 460 cp (0.46 Pa.s) | |

This thickened oil is applied on moist and dirty hair. It possesses good foaming and detergent power and permits to obtain untangling of moistened hair and an ease in shaping or styling the hair.

Example F2

Care for African type hair

The composition has the following formulation:

| | |
|---|---|
| Polymer according to Example 15 | 1.25 g |
| Polymer according to Example 16 | 1.25 g |
| Light petrolatum oil, HZ No. 25, sold by Geeraert Matthys | 57.5 g |
| Cyclopentadiemthylsiloxane, sold under the designation "SILBIONE HUILE 700 45 V5", by Rhone Poulenc | 40.0 g |
| Viscosity of the composition - 650 cp (0.65 Pa.s) | |

This product is provided in the form of a transparent gel and is applied onto moistened hair. It facilitates untangling and imparts softness and shine to dry hair.

Example F3

Capillary protecting oil

This composition has the following formulation:

| | |
|---|---|
| Polymer according to Example 15 | 1.0 g |
| Polymer according to Example 16 | 1.0 g |
| Isoparaffinic hydrocarbons, sold under the designation, "ISOPARH" by Exxon | 57.0 g |
| Cyclopentadimethylsiloxane, sold under the designation, "SILBIONE HUILE 700 45 V5", by Rhone Poulenc | 40.0 g |
| 2-hydroxy-4-methoxybenzophenone, sold under the designation, "UVINUL M40" by BASF | 1.0 g |

Viscosity of the composition—3100 cp (3.1 Pa.s)

This oil has a gelled appearance and is applied to wet hair. After rinsing, the hair is soft and smooth.

Example F4

Perfumed bath foaming oil

This composition has the following formulation:

| | |
|---|---|
| Polymer according to Example 15 | 1.5 g |
| Polymer according to Example 16 | 1.5 g |
| 50/50 monoisopropanol amine lauryl ether sulfate/diethanolamide of copra acid mixture, sold under the designation, "TEXAPON WW 99" by Henkel | 40.0 g |
| Sorbitan monolaurate oxyethylenated with 20 moles of ethylene oxide, sold under the designation "TWEEN 20" by ICI | 5.0 g |
| Virgin sesame oil | 25.0 g |
| 4-ditert. butyl hydroxytoluene | 0.1 g |
| 4-tert. butyl hydroxyanisole | 0.04 g |
| Propyl parahydroxybenzoate | 0.15 g |
| Perfume | 1.0 g |
| Deodorized, raffinated colza oil, sufficient amount for | 100 g |

This bath oil is employed in a bath tub at a rate of 10 g/100 l of water.

It imparts to the skin at the end of the bath softness and a satiny appearance.

Example F5

Makeup foundation (w/o emulsion)

This composition has the following formulation:

| | |
|---|---|
| Polymer according to Example 15 | 0.15 g |
| Polymer according to Example 16 | 0.15 g |
| Isopropyl myristate | 11.00 g |
| Petrolatum | 4.00 g |
| P.E.G. 7 hydrogenated castor oil | 3.00 g |
| Beeswax | 7.50 g |
| Paraben | 0.12 g |
| 4-tert. butyl hydroxyanisole (BHA) | 0.15 g |
| Iron oxide | 1.50 g |
| Titanium oxide | 11.50 g |
| Octyldimethyl PABA* | 1.00 g |
| Cyclomethicone | 9.50 g |
| Water | 38.35 g |
| Propylene glycol | 4.00 g |
| Diazolidinyl urea | 0.20 g |
| Magnesium sulfate | 0.70 g |
| Cornstarch | 7.00 g |
| Phenylethyl alcohol | 0.18 g |
| Total | 100 g |

*PABA: 2-ethylhexyl paradimethylaminobenzoate

Example F6

Makeup foundation

The same formulation as in Example F5 with the polymer combination:

| | |
|---|---|
| Polymer according to Example 3 | 0.15 g |
| Polymer according to Example 16 | 0.15 g |

Example F7

Lip rouge

| | |
|---|---|
| Polymer according to Example 3 | 0.30 g |
| Polymer according to Example 16 | 0.30 g |
| Octyl hydroxystearate | 13.20 g |
| Octyl stearate | 6.60 g |
| Ricin oil | 6.60 g |
| Petrolatum oil | 13.20 g |
| 3,5-d-tert. butyl-4-hydroxy toluene (BHT) | 0.10 g |
| Lanolin | 22.60 g |
| Vinylacetate/allyl stearate copolymer | 11.30 g |
| Carnauba wax | 2.80 g |
| Microcrystalline wax | 11.30 g |
| FD&C Yellow No. 6 | 7.30 g |
| D&C Red No. 7 | 2.00 g |
| Iron oxide | 1.50 g |
| Titanium oxide | 0.65 g |
| Perfume | 0.25 g |
| Total | 100 g |

Example F8

Mascara

| | |
|---|---|
| Paraffin wax | 27.7 g |
| Stearic acid | 3.8 g |
| Starch | 1.3 g |
| Iron oxide | 6.3 g |
| Isoparaffin | 59.6 g |
| Polymer according to Example 16 | 0.65 g |
| Polymer according to Example 15 | 0.65 g |

Example F9

Makeup remover oil

| | |
|---|---|
| Solution A: Isohexadecane | 48.75 g |
| Lauryl acrylate/methacrylic acid copolymer, according to Example 3 | 1.5 g |
| Solution B: Isohexadecane | 48.75 g |
| Stearyl methacrylate/DAMEMA, according to Example 16 | 1 g |

Operating procedure:

Solutions A and B are prepared at 80° C. with magnetic stirring.

When A and B are clear, they are gently mixed at 80° C. with magnetic stirring. Stirring is continued at this temperature for about 2 hours.

The stirring is discontinued and the product is permitted to cool to ambient temperature. A transparent oily gel is obtained.

Example F10

Solar formulation

| | |
|---|---|
| Polymer according to Example 3 | 1.25 g |
| Polymer according to Example 16 | 1.25 g |
| 3',5'-di.tert.butyl-4'-hydroxy-3-benzylidene camphor | 1.5 g |
| "FINSOLV TN", sufficient amount for | 100 g |

Example F11

After-sun formulation

| | |
|---|---|
| Polymer according to Example 16 | 1 g |
| Polymer according to Example 3 | 1.5 g |
| Bisabolol | 0.5 g |
| Petrolatum oil, sufficient amount for | 100 g |

Example F12

Solar formulation with UVA filter

| | |
|---|---|
| Polymer according to Example 16 | 1.5 g |
| Polymer according to Example 15 | 1 g |
| "PARSOL 1789", (Tert.butyl methoxy-dibenzoylmethane), sold by Givaudan | 1.25 g |
| Isopropyl myristate | 20 g |
| Petrolatum oil, sufficient amount for | 100 g |

Example F13

Solar formulation with UVB filter

| | |
|---|---|
| Polymer according to Example 3 | 1.125 g |
| Polymer according to Example 16 | 0.75 g |
| "WITICONOL APM"* | 24 g |
| "UNINUL TI50", (2,4,6-trianilino-paracarbo-2'-ethylhexyl-1'-oxy-1,3,5-triazine) | 1 g |
| "PARLEAM"**, sufficient amount for | 100 g |

*(Propylene glycol ether of myristic alcohol), sold by Witco Organics
**(hydrogenated polyisobutane), sold by Nippon Oil

Example F14

Solar formulation with polymer filter

| | |
|---|---|
| Polymer according to Example 16 | 1.25 g |
| Polymer according to Example 3 | 1.25 g |
| Homopolymer derived from polyacrylamide containing units of Formula I | 1.25 g |
| Palmitic ester of 2-ethyl hexyl glycerol ether, sufficient amount for | 100 g |

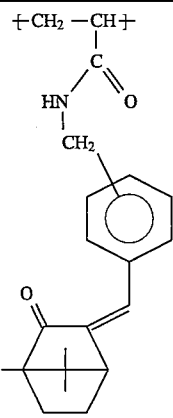

Formula I

Example F15

Solar formulation with polymer filter

| | |
|---|---|
| Polymer according to Example 16 | 1.5 g |
| Polymer according to Example 15 | 1.5 g |
| Homopolymer derived from polyacrylamide containing units of Formula II | 1.5 g |
| Isopropyl myristate, sufficient amount for | 100 g |

Formula II

Example F16

Anti-mosquito oil

| | |
|---|---|
| Polymer according to Example 15 | 1.0 g |
| Polymer according to Example 16 | 1.0 g |
| Citronella essential oil | 10.0 g |
| Volatile silicone 700 45 V5, by Rhone Poulenc, sold under the designation "CYCLOMETHICONE" | 40.0 g |
| Petrolatum oil, sufficient amount for | 100 g |

Example F17

Anti-inflammatory gel containing a corticoid in a lipophilic medium

| | |
|---|---|
| "PARLEAM" | 67.78 g |
| Isopropyl myristate | 30 g |
| Polymer according to Example 15 | 1 g |
| Polymer according to Example 16 | 1 g |
| Hydrocortisone 17 butyrate | 0.2 g |
| BHA | 0.002 g |

Example F18

Gel for the treatment of psoriasis containing dithranol

| | |
|---|---|
| Fluid petrolatum oil | 60.4 g |
| Cyclomethicone | 35 g |
| Polymer according to Example 3 | 1.75 g |
| Polymer according to Example 16 | 1.75 g |
| Dithranol | 1 g |
| BHA | 0.05 g |
| BHT | 0.05 g |

Example F19

Solar formulation

| | |
|---|---|
| Polymer according to Example 3 | 0.5 g |
| Polymer according to Example 16 | 0.5 g |
| 3',5'-di.tert.butyl-4'-hydroxy-3-benzylidene camphor | 0.5 g |
| "SINNOWAX AO" | 3 g |
| Nonselfemulsifiable mixture of glycerol mono- and distearate | 1 g |
| Cetyl alcohol | 1 g |
| Silicone oil 700 47V 300 | 1 g |
| "FINSOLV TN" | 10 g |
| Glycerine | 20 g |
| Preservative, sufficient amount | |
| Purified water, sufficient amount for | 100 g |

Example F20

After sun formulation

| | |
|---|---|
| Polymer according to Example 16 | 0.75 g |
| Polymer according to Example 15 | 0.75 g |
| Bisabolol | 0.5 g |
| "SINNOWAX AO" | 3 g |
| Nonselfemulsifiable mixture of glycerol mono and distearate | 1 g |
| Cetyl alcohol | 1 g |
| Petrolatum oil | 9 g |
| Glycerine | 20 g |
| Preservative, sufficient amount | |
| Purified water, sufficient amount for | 100 g |

Example F21

Antisolar formulation

| | |
|---|---|
| Titanium oxide coated with alumina and aluminum stearate, sold under the trade name "MICRO TIO$_2$ MT 100T" by Tayca | 5 g |
| Polymer according to Example 16 | 0.4 g |
| Polymer according to Example 3 | 0.4 g |
| "ARLACEL 780" | 5 g |
| Petrolatum oil | 14 g |
| "FINSOLV TN" | 6 g |
| Glycerine | 4 g |
| Magnesium sulfate | 0.7 g |
| Preservative, sufficient amount | |
| Purified water, sufficient amount for | 100 g |

Example F22

Antisolar formulation

| | |
|---|---|
| "UVINUL T150" | 1 g |
| Polymer according to Example 16 | 0.6 g |
| Polymer according to Example 15 | 0.6 g |
| "ARLACEL 780" | 5 g |
| "WITCONOL APM" | 20 g |
| Glycerine | 4 g |
| Magnesium sulfate | 0.7 g |
| Preservative, sufficient amount | |
| Purified water, sufficient amount for | 100 g |

Example F23

Antisolar formulation

| | |
|---|---|
| "PARSOL 1789" | 1.5 g |
| Polymer according to Example 16 | 1 g |
| Polymer according to Example 3 | 1 g |
| Isopropyl myristate | 20 g |
| Preservatives, sufficient amount | |
| "ARLACEL 780" | 5 g |
| Purified water, sufficient amount for | 100 g |

Examples F24 to F27

Gelled preparations

PA1: polymer obtained starting with monomers: stearyl methacrylate, methacrylic acid, lauryl acrylate (56.6:3.4:40)

PA2: polymer obtained starting with monomers: lauryl acrylate, methacrylic acid (96.6:3.4)

Using these polymers the following gelled preparations (F24 to F27) are obtained:

| Example F: | 24 | 25 | 26 | 27 |
|---|---|---|---|---|
| PA1 | 1.165 | 1.75 | 1.165 | 0.6 |
| PA2 | 1.165 | 1.75 | 1.165 | 1.2 |
| Polymer of Example 2 | 2.34 | 3.5 | 2.34 | 1.8 |
| Petrolatum oil | 72 | 69.5 | 38.17 | 28.6 |
| Stearyl octanoate and isopropyl myristate (90/10) | 0 | 0 | 33.66 | 0 |
| (DUB liquid 85 IP of STEARINERIES, by Dubois) Volatile silicone (D.C. Fluide 245) | 0 | 0 | 0 | 25 |
| Caprylic/capric triglycerides (MYGLIOL 812, by Huls) | 0 | 0 | 0 | 26.3 |
| 2-octyl dodecylether, oxyethylenated with 25 ethylene oxide units, sold under the trade name "EMALEX OD-25" by Nihon Emulsion | 9.33 | 9.4 | 9.4 | 7 |
| Water | 9.33 | 9.4 | 9.4 | 6 |
| Glycerol | 4.67 | 4.7 | 4.7 | 3.5 |

These gels (F24 to F27) are flexible on solidification and are easily spread. They are used preferably in emulsion to thicken and stabilize them as indicated below.

Example F28

Water-in-oil Emulsion

| Phase A | |
|---|---|
| (50/50) magnesium lanolate-petrolatum oil, sold under the trade name "MEXANYL GO" by Chimex | 5.7 g |
| Hydrogenated lanolin, sold under the trade name "SUPERSAT" by Rita | 6.65 g |
| 2-ethylhexylglycerylether palmitate (octoxyglyceryl palmitate) | 2 g |
| (15/85) lanolin alcohol-petrolatum oil, sold under the trade name "AMERCHOL 101" by Amerchol | |
| Petrolatum oil | 9.25 g |
| Stearyl octanoate - isopropyl myristate, (90/10), sold under the trade name "DUB LIQUIDE 85 IP" by Stearineries de Dubois | 7.95 g |
| Phase B | |
| Water | 50.45 g |
| Phase C | |
| Gelled preparation F24 | 15 g |

Fatty phase A is prepared and the water (phase B) is added. When the emulsion is formed, there is introduced into it phase C at a temperature lower than 40° C. with mild stirring. A white cream that is agreeable to spread is obtained.

Example F29

Emulsion

| Phase A | |
|---|---|
| Sorbitan isostearate, sold under the trade name "ARLACEL 987" by ICI | 5 g |
| Petrolatum oil | 15.4 g |
| Propylene glycol | 3 g |
| Phase B | |
| Magnesium sulfate | 0.6 g |
| Water | 65 g |
| Phase C | |
| Gelled preparation F25 | 11 g |

Fatty phase A is prepared and then aqueous phase B is added. After obtaining the emulsion, there is introduced into it phase C at a temperature lower than 40° C. with mild stirring. A white cream agreeable on application and which penetrates well is obtained.

Example F30

Water-in-oil emulsion

| Phase A | |
|---|---|
| Isostearyl succinate mono-diglyceryl, sold under the trade name "INWITOR 780K" by Huls | 5 g |
| Petrolatum oil | 11.2 g |
| Caprylic-capric triglyceride, sold under the trade name "MYGLIOL 812" by Huls | 9.3 g |
| Volatile silicone (D.C. FLUID 245) | 4.5 g |
| Phase B | |
| Water | 48 g |
| Magnesium sulfate | 2 g |
| Glycerol | 3 g |
| Cornstarch | 7 g |
| Phase C | |
| Gelled preparation F27 | 10 g |

This cream is prepared as indicated in the preceding examples. A white and unctuous cream, agreeable to use, is obtained.

Example F31

Water-in-oil emulsion

| Phase A | |
|---|---|
| Isostearyl succinate mono-diglyceryl, sold under the trade name "INWITOR 780K" by Huls | 5 g |
| Polyphenyl methyl siloxane, sold under the trade name "SILBIONE 70633V30" by Rhone Poulenc | 7 g |
| Caprylic-capric triglyceride, sold under the trade name "MYGLIOL 812" by Huls | 10 g |
| Volatile silicone (D.C. Fluid 245) | 8.0 g |
| Phase B | |
| Water | 45 g |
| Magnesium sulfate | 2 g |
| Glycerol | 3 g |
| Cornstarch | 10 g |
| Phase C | |
| Gelled preparation F26 | 10 g |

This cream is prepared as indicated in the preceding examples. A white, unctuous cream, cool on application is obtained.

Examples F32 to F34

Makeup remover gels, rinsable with water

| | (in grams) | | |
|---|---|---|---|
| Example F | 32 | 33 | 34 |
| Phase A | | | |
| PA1 | 0.25 | 1.5 | 0.25 |
| PA2 | 0.75 | 0 | 0.75 |
| Polymer according to Example 2 | 1 | 1.5 | 1 |
| Petrolatum oil | 2 | 3 | 2 |
| Jojoba oil | 78 | 78 | 71 |
| Volatile silicone (D.C. 245) | 0 | 0 | 5 |
| Phase B | | | |
| Oxyethylenated octyldecylether (25 EO), sold under the trade name "EMALEX OD 25" by Nihon Emulsion | 5 | 4 | 5 |
| Water | 5 | 4 | 5 |
| Glycerol | 4 | 4 | 5 |
| Oxyethylenated sorbitan oleate (40 EO), sold under the trade name "ARLATONET" by ICI | 4 | 4 | 4 |
| Glucoside decylether, sold under the trade name "ORAMIX NS 10" by Seppic | 0 | 0 | 1 |

These gels are prepared by slowly introducing phase A, heated to 60° C., into melted phase B. The mixture is vigorously stirred until a gel is obtained which is rapidly cooled with mild stirring.

The resulting gels, rich in jojoba oil, are particularly comfortable to use. During use, they are applied to dry or moist skin which is lightly massaged to resorb the makeup. The skin is rinsed with water.

Example F35

Makeup remover gel

|  | (in grams) |
|---|---|
| Phase A | |
| PA1 | 0.25 |
| PA2 | 0.75 |
| Polymer of Example 2 | 1 |
| Petrolatum oil | 2 |
| Jojoba oil | 72 |
| Volatile silicone (D.C. 245) | 5 |
| Phase B | |
| Oxyethylenated octyldodecylether (20 EO), sold under the trade name "EMALEX OD 20" by Nihon Emulsion | 5 |
| Water | 5 |
| Glycerol | 5 |
| Oxyethylenated sorbitan oleate, (40 EO), sold under the trade name "ARLATONET" by ICI | 4 |

The operating procedure is the same as that for the preceding examples. The resulting gel has the same properties.

Examples F36 to F39

Makeup remover gels

| | (in grams) | | | |
|---|---|---|---|---|
| Example F | 36 | 37 | 38 | 39 |
| Phase A | | | | |
| PA1 | 0.4 | 0.07 | 0.25 | 0.25 |
| PA2 | 1.25 | 0.215 | 0.75 | 0.75 |
| Polymer of Example 2 | 1.65 | 0.285 | 1 | 1 |
| Petrolatum oil | 3.3 | 72 | 7 | 35.26 |
| Jojoba oil | — | 15.15 | 10 | 1 |
| Hydrogenated isoparaffin, sold under the trade name "PARLEAM" by Nippon Oil | 37.7 | — | — | — |
| 2-ethylhexyl palmitate, sold under the trade name "CERAPHYL 368" by Mallinckrodt | 37.7 | 5.7 | 60 | 30.5 |
| Stearyl octanoate and isopropyl myristate, (90/10), sold under the trade name "DUB LIQUIDE 85 IP" by Stearineries Dubois | — | — | — | — |
| Volatile silicone (D.C. Fluid 245) | — | — | — | 10 |
| Perfume | — | — | — | 0.2 |
| Phase B | | | | |
| Oxyethylenated octyldodecylether, (25 EO), sold under the trade name "EMALEX OD 25" by Nihon Emulsion | 4.8 | 1.43 | 5 | 4.5 |
| Water | 5.7 | 1.14 | 5 | 4.5 |
| Glycerol | 3.8 | 1.71 | 6 | 6 |

| | (in grams) | | | |
|---|---|---|---|---|
| Example F | 36 | 37 | 38 | 39 |
| Oxyethylenated sorbitan oleate (40 EO), sold under the trade name "ARLATONE T" by ICI | 3.8 | 1.14 | 4 | 4 |
| Antioxidant | — | 0.01 | — | 0.04 |

These gels are prepared in accordance with the procedures described previously.

Makeup remover gels are obtained which are particularly comfortable to use and provide rapid and effective makeup removal. These gels, tested on users, have been favorably appreciated.

As an example, gel F39 was judged by a panel of 16 women who found it easy and quick to apply, who have judged its makeup removal power very good and who have noted a sensation of comfort after makeup removal (absence of fatty film, soft and clean skin).

Example F40

Rinsable hydrating mask

| | |
|---|---|
| Phase A | |
| PA1 | 0.5 g |
| PA2 | 1.5 g |
| Polymer of Example 2 | 2 g |
| Petrolatum oil | 25 g |
| Apricot kernel oil | 10 g |
| Volatile silicone (D.C. Fluid 245) | 20 g |
| Phase B | |
| Eastman AQ 55 S polymer (polyester, polyisophthalate) | 2 g |
| Oxyethylenated octyldodecyl ether, (25 EO), sold under the trade name "EMALEX OD 25" by Nihon Emulsion | 7 g |
| Water | 7 g |
| Glycerol | 24 g |
| Oxyethylenated sorbitan oleate, (40 EO), sold under the trade name "ARLATONE T" by ICI | 1 |

This mask is prepared according to the procedures described above for the makeup remover gels.

A translucent gel is obtained that is applied as a mask on the face. After 5 to 10 minutes of application, the face is rinsed with water.

Example F41

Oil-based body gel

Gelled preparation for dry skin rich in emollient oils, penetrating well and not leaving an oily film on the skin is prepared. This composition exhibits the advantage of not being required to be rinsed after application, while containing a large amount of oil.

Example F42

Capillary gel to be rinsed after application.

This gel nourishes and sheaths the hair and improves its styling.

| Example F | 41 | 42 |
|---|---|---|
| | (in grams) | |
| PA1 | 0.25 | 0.5 |
| PA2 | 0.75 | 2 |
| Polymer of Example 2 | 1 | 2.5 |
| Capric and caprylic triglycerides, sold under the trade name "MIGLYOL 812" by Huls France | 7 | — |
| Propylene glycol dicaprylate, sold under the trade name "CRODAMOL PC" by Croda | 20 | — |
| Isostearyl neopentanoate, sold under the trade name "CERAPHYL 375" by Mallinckrodt | 6 | — |
| Squalene (Johan Martens) | 6 | 9 |
| Diisopropyl dimerdilinoleate (Schercemol DID-SCHER) | — | 15 |
| Volatile silicon (D4) (Dow Corning Fluid 244 | 30 | — |
| Volatile silicone (D5) (Dow Corning Fluid 245) | 20 | 48 |
| Silicone gum (Dow Corning QC F2-1671) | — | 3 |
| Octyldodecylether of ethylene oxide (25 EPO), sold under the trade name "EMALEX OD 25" by Nihon Emulsion | 2 | 4 |
| Water | 3 | 5 |
| Glycerol | 4 | 7 |
| Oxyethylenated sorbitan oleate, (40 EO), sold under the trade name "ARLATONE T" by ICI | — | 4 |

We claim:

1. A thickened cosmetic composition containing an oil phase and a thickening agent for said oil phase, said thickening agent comprising in combination:

(1) a first copolymer consisting essentially of (a) units resulting from the polymerization of an unsaturated ester of a long chain fatty alcohol and (b) units resulting from the polymerization of a monomer selected from the group consisting of unsaturated monocarboxylic acid, unsaturated dicarboxylic acid, monoester of unsaturated dicarboxylic acid, monoamide of unsaturated dicarboxylic acid and unsaturated sulfonic acid, and (2) a second copolymer consisting essentially of (a) units resulting from the polymerization of an unsaturated ester of a long chain fatty alcohol and (b) units having the following formula:

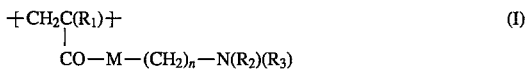

wherein

M represents —O— or —NH—, $R_1$ represents —H or —$CH_3$, n is a number ranging from 2 to 20, and $R_2$ and $R_3$, each independently, represent hydrogen or a hydrocarbon having 1–4 carbon atoms, or units resulting from the polymerization of a monomer selected from the group consisting of acrylamide, methacrylamide, N,N-dimethylacrylamide, N-vinylpyrrolidone, and diacetone acrylamide, the weight amount of units 1(a) and 2(a) in said first and second copolymers being at least equal to 50%, and the weight amount of said units 1(b) and 2(b) in said first copolymer and second copolymer being at least equal to 2%.

2. The cosmetic composition of claim 1 wherein said unsaturated monocarboxylic acid is selected from the group consisting of acrylic acid, methacrylic acid and crotonic acid.

3. The cosmetic composition of claim 1 wherein said unsaturated dicarboxylic acid is selected from the group consisting of maleic acid and itaconic acid.

4. The cosmetic composition of claim 1 wherein said monoester of unsaturated dicarboxylic acid is an ester from an alcohol having 1–22 carbon atoms.

5. The cosmetic composition of claim 1 wherein said monoamide of unsaturated dicarboxylic acid is an amide from an amine having 1–22 carbon atoms.

6. The cosmetic composition of claim 1 wherein said unsaturated sulfonic acid is selected from the group consisting of 2-acrylamido-2-methyl propanesulfonic acid and 2-sulfoethyl methacrylate.

7. The cosmetic composition of claim 1 wherein said units of formula (I) result from the polymerization of a monomer selected from the group consisting of dimethylaminoethyl methacrylate, diethylaminoethyl acrylate and N-dimethylaminopropyl methacrylate.

8. The cosmetic composition of claim 1 wherein the relative weight amounts of said first and second copolymers range from 10:90 to 90:10.

9. The cosmetic composition of claim 1 wherein the relative weight amounts of said first and second copolymers range from 25:75 to 75:25.

10. The cosmetic composition of claim 1 wherein said thickening agent is present in a proportion between 0.1 and 10% by weight of said composition.

11. The cosmetic composition of claim 1 wherein said thickening agent is present in a proportion between 0.5 and 5% by weight of said composition.

12. The cosmetic composition of claim 1 wherein the oil phase contains at least 55% by weight of an oil or a mixture thereof.

13. The cosmetic composition of claim 1 which also contains a nonionic amphiphilic agent selected from the group consisting of polyoxyethylenated ester of a fatty acid and sorbitan, polyoxyethylenated ester of fatty acid and glycerol, polyoxyethylenated ester of a fatty acid and propylene glycol, polyoxyethylenated alkyl ether, polyoxypropylenated alkyl ether, a polyoxyethylenated alkyl phenyl ether, polyoxypropylenated alkyl phenyl ether and polyoxyethylenated Guerbet alcohol.

14. The cosmetic composition of claim 13 wherein said nonionic amphiphilic agent is present in a proportion between 1 to 10% by weight based on the weight of said oil phase.

* * * * *